(12) United States Patent
Tsao

(10) Patent No.: US 6,467,982 B1
(45) Date of Patent: Oct. 22, 2002

(54) EASILY OPENED ELONGATED TUBULAR CONTAINER

(76) Inventor: Chien-Hwa Tsao, 4F, No. 5, Alley 17, Lane 17, Shin Yi Rd., Yunghe City, Taipei Hsien (TW)

( * ) Notice: Subject to any disclaimer, the term of this patent is extended or adjusted under 35 U.S.C. 154(b) by 0 days.

(21) Appl. No.: 09/694,383

(22) Filed: Oct. 24, 2000

(30) Foreign Application Priority Data

Oct. 28, 1999 (TW) .................................... 088218304

(51) Int. Cl.[7] ............................................. A61M 35/00
(52) U.S. Cl. ........................... 401/263; 401/205; 604/2
(58) Field of Search ................................ 401/205, 263; 604/1, 2; 222/563

(56) References Cited

U.S. PATENT DOCUMENTS

| | | | | |
|---|---|---|---|---|
| 2,100,157 A | * | 7/1937 | Chandler | 401/205 |
| 3,519,364 A | * | 7/1970 | Truhan | 604/2 |
| 4,820,259 A | * | 4/1989 | Stevens | 604/2 |
| 5,947,986 A | * | 9/1999 | Lewis | 604/2 |

FOREIGN PATENT DOCUMENTS

DE 297 13 303 U1 * 10/1997

* cited by examiner

Primary Examiner—Charles R. Eloshway
(74) Attorney, Agent, or Firm—Rosenberg, Klein & Lee

(57) ABSTRACT

An easily opened, elongated tubular container is disclosed. The container is composed of an inner tube having at least one open end and being adapted for filling with various liquid substances. An outer tube, relatively reciprocative with respect to the inner tube, and having at least one sealing element capable of sealing the open end of the inner tube is provided, and at least one attachment is installed at the exit open end of the outer tube. The sealing element, which is formed as one piece with the outer tube, closes the opening of the inner tube. The outer tube is displaceable, by the operator, from a position which closes the open end of the inner tube to the reverse position which releases the open end of the inner tube so that the liquid in the inner tube is released to flow out the open end and be absorbed by the attachment.

15 Claims, 11 Drawing Sheets

EASILY OPENED ELONGATED TUBULAR CONTAINER

BACKGROUND OF THE INVENTION

1. Field of the Invention

The present invention relates to an easily opened elongated tubular container, and more particularly, to a secure, clean, and easily handled and opened elongated tubular container.

2. Description of the Prior Art

For treatment of minor trauma, it is common to apply liquid medicine to the wounds using a cotton swab moistened with the medicine from medicine vials. Such a method of treatment has several disadvantages, in that, for example, it is quite inconvenient to prepare a lot of medicine vials of every size, especially during a long distance tour or during outdoor activities. Furthermore, the medicine stored in a large container is susceptible to contamination or deterioration by frequency contact with the outside atmosphere or foreign materials, such as cotton swabs or spoons, which may cause the liquid medicine to vary its concentration through evaporation.

Similarly, perfumes, drinks, and seasonings encounter the same problems for storage as described above. If the container is too bulky, it is inconvenient to carry along, and specially made tools must be used to take them out. The inherent disadvantages described above such as contamination, deterioration, evaporation, and drying up will discourage customers. Some improvements must be made to overcome such disadvantages.

In view of the foregoing situation, the inventor of the present invention herein conducted extensive research based on many years of experience gained through professional engagement in the manufacturing of related products, with continuous experimentation and improvement culminating in the development of the improved structure of easily opened elongated tubular containers of the present invention.

SUMMARY OF THE INVENTION

It is a first object of the present invention to provide an easily opened elongated tubular container which can store medicine, cosmetics, liquid, food and drinks therein, the content being completely isolated from the environment before use, thereby preventing deterioration from being contacted with the atmosphere, thus extending the expected life span of the content. When the content in the container is to be used, the user may open the container with only his hand without the aid of any extra tool, and the liquid therein will flow out smoothly in a wholesome state.

It is a second object of the present invention to provide an easily opened elongated tubular container having both ends substantially sealed before use so that the content never leaks out without application of external means, thus leading to the advantage that there is no limit to the size of the openings so that the application field of the container is unlimited.

It is a third object of the present invention to provide an easily opened elongated tubular container such that the user may, according to actual requirements, optionally select attachments or tools of different kinds and sizes; for example, a sterilized cotton swab, a spoon, an agitator, or a brush to promptly contact the opened top end of the container for various applications.

It is a fourth object of the present invention to provide an easily opened elongated tubular container which is simply constructed, easily operable so as to facilitate the liquid content to automatically flow out in adequate amounts through air exchange in the container caused by the rapid opening of both ends thereof without squeezing the container by hand.

These and other objects of the present invention are achieved by providing an easily opened elongated tubular container composed of an inner tube, having at least one open end available for filling with various liquid substances; for example, medicines, cosmetics, perfumes, food and drinks, seasonings, and detergents, etc.; and an outer tube relatively reciprocative with respect to the inner tube and having at least one sealing element capable of sealing the open end of the inner tube; and at least one attachment installed at the open end of the outer tube. The sealing element, which is formed as one piece with the outer tube or, alternatively, is separately formed, normally closes the opening of the inner tube in a sealed state. However, the outer tube is displaceable by the operator from a position where the open end of the inner tube is closed to the other position where the open end of the inner tube is released so that the liquid filling the inner tube is released to flow out of the open end and is absorbed by the attachment installed at the exit open end of the outer tube.

BRIEF DESCRIPTION OF THE DRAWINGS

To enable a further understanding of the innovative and technological content of the invention herein, refer to the detailed description of the invention and the accompanying brief description of the drawings appended below.

DETAILED DESCRIPTION OF THE PREFERRED EMBODIMENT

Figure 1:
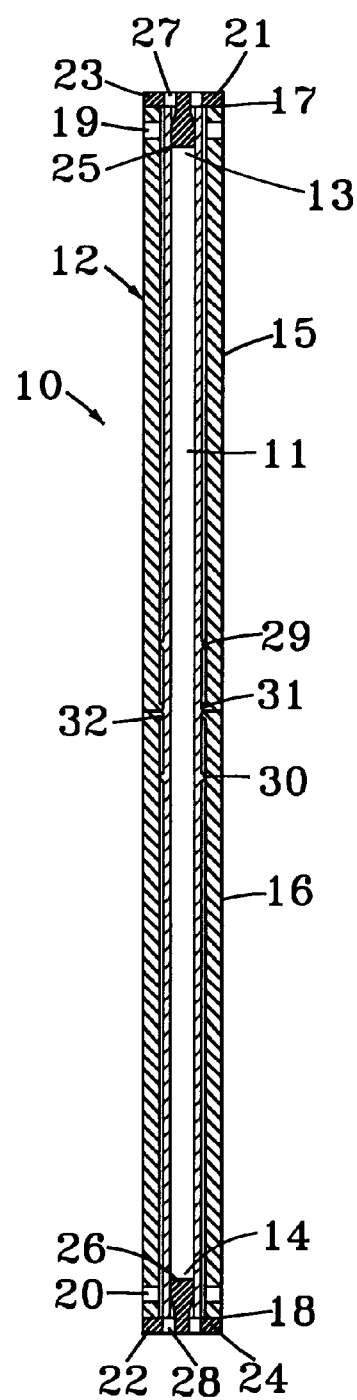
FIG. 1 is a lengthwise cross-sectional view wherein the container is in the closed state in a first embodiment of the present invention.

Referring to FIG. 1, in the first embodiment of the present invention, the easily opened elongated tubular container comprises an inner tube for filling with various liquid substances, such as medicines, perfumes, cosmetics, food and drinks, seasonings, and detergents; and an outer tube 12 clad over the inner tube 11 and reciprocative with respect to the inner tube 11 along the lengthwise direction.

The inner tube 11 is formed into a slender straight tube made of non-poisonous plastics or other harmless materials. In the first embodiment, the inner tube 11 has two open ends 13 and 14 respectively at its two ends thereof. The inner tube 11 therefore can be formed of relatively simple and low production cost processes, for example, through extrusion, ejection, or other equivalent processes.

In the first embodiment, the outer tube 12 is divided into two separate tubular sections 15 and 16, both made of plastics or other equivalent non-poisonous materials, each with an open end 17(18). The inner diameter of the two sections 15, 16 is slightly greater than the outer diameter of the inner tube 11 so as to accommodate the inner tube 11 within the two outer tubular sections 15, 16. A through hole 19 or 20 may optionally be bored near the open end 17 or 18. First and second sealing elements 21 and 22 are respectively attached to the top fringes of open ends 17 and 18 through proper binding means. The lengthwise cross-section of the first and the second sealing elements 21, 22 is configured in a T-shape, and each sealing element 21(22) has an annularly protruded lip portion 23(24) extending a width approximately equal to the outer diameter of the tubular section 15(16). As shown in FIG. 1, when the two tubular sections 16 and 16 approach each other, the stem portions 25, 26 of the sealing elements 21, 22 tightly plug into the two open ends 13, 14 of the inner tube space 11, thereby prohibiting the liquid content stored therein to flow out unexpectedly.

The inner tube 11, enclosed in the tubular sections 15, 16, is provided with two outwardly protruded skid flanges 29, 30, which face each other on the outer circumferential wall surface. The tubular sections 15, 16 are provided with inwardly extended positioning flanges 31, 32, respectively, at their inner open ends for mating respectively with the protruded skid flanges 29, 30 such that the tubular sections 15, 16 are able to reciprocate between the retracted position (FIG. 1) and the extended position (FIG. 2).

When the tubular sections 15, 16 are located at the retracted position shown in FIG. 1, their inner open ends approach and mate with each other causing the stem portions 25, 26 of the sealing elements 21, 22 to tightly seal the two open ends 13, 14 of the inner tube 11, thereby prohibiting the liquid content stored therein to flow out.

Figure 2:
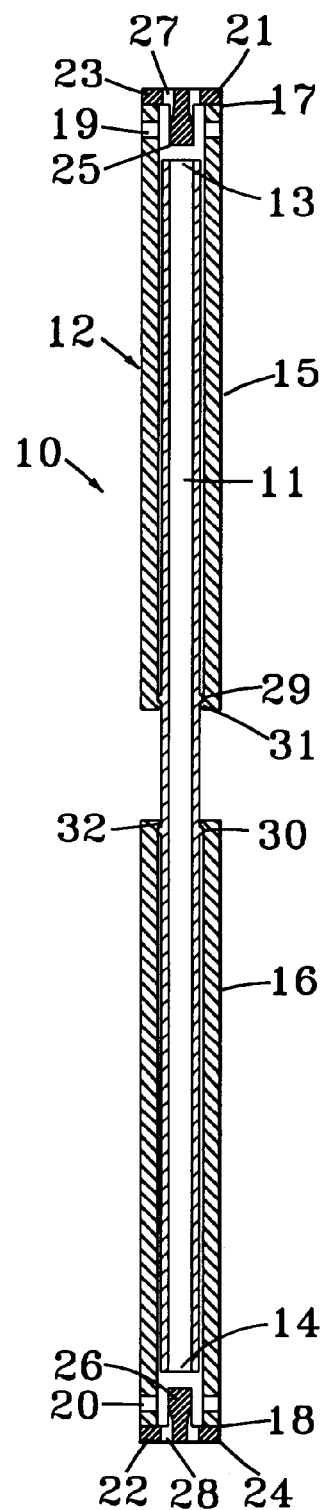
FIG. 2 is a lengthwise cross-sectional view wherein the container is in the opened state in a first embodiment of the present invention.

When the tubular sections 15, 16 are pulled away from each other and displaced to the extended position shown in FIG. 2, the positioning flanges 31, 32 of the tubular sections 15, 16 are respectively held by the skid flanges 29, 30 of the inner tube 11 without slipping. At the same time, the first and the second sealing elements 21, 22 are respectively removed from the open ends 13, 14 of the inner tube 11 so that the liquid content stored therein is able to flow or ooze out from the open ends 13, 14 to the through holes 19, 20 of the tubular sections, and to the liquid exuding holes 27, 28 on the first and the second sealing elements 21, 22.

Figure 3:
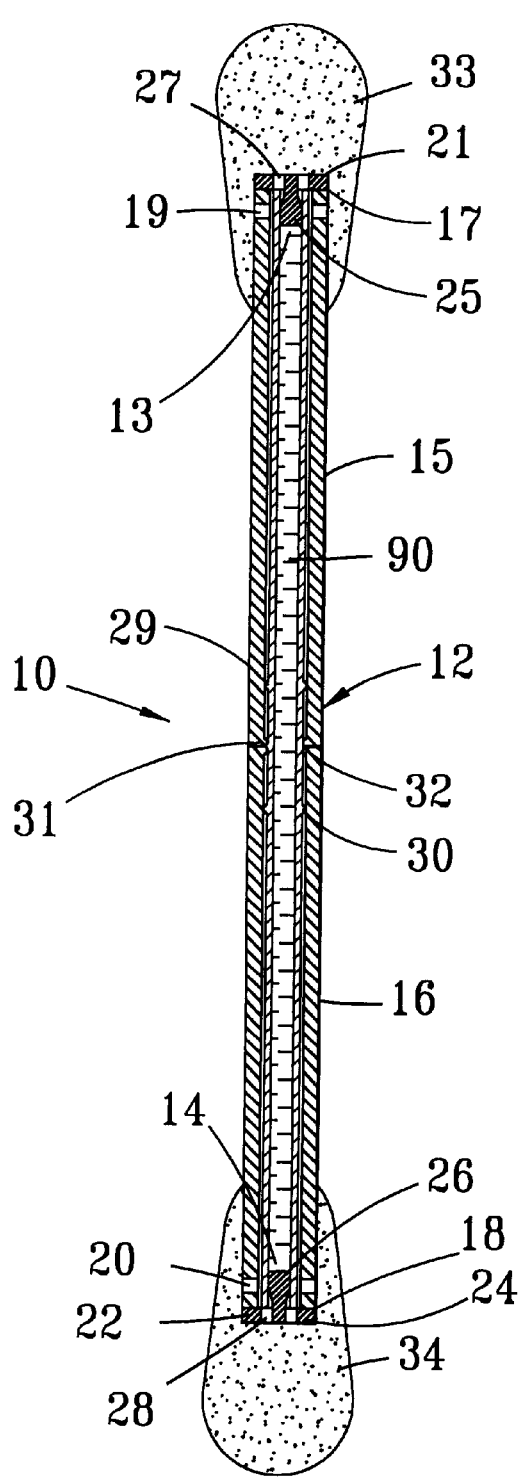
FIG. 3 is a lengthwise cross-sectional view wherein the container is in the closed state in a second embodiment of the present invention.
Figure 4:
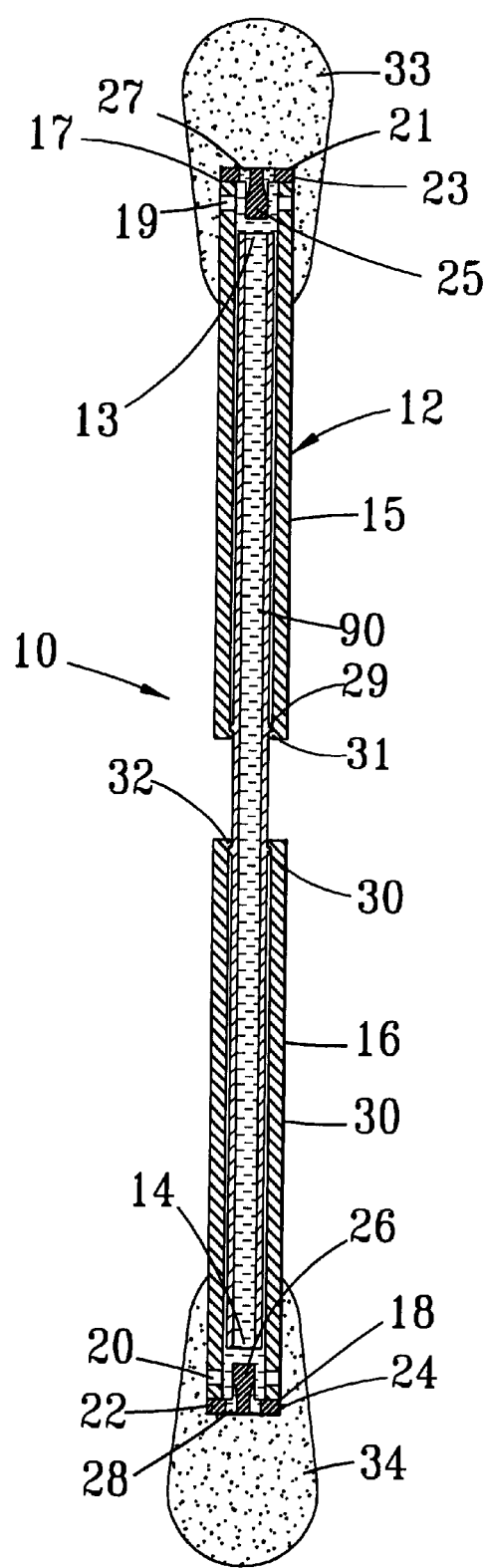
FIG. 4 is a lengthwise cross-sectional view wherein the container is in the opened state in a second embodiment of the present invention.

Referring to FIGS. 3 and 4, in the second embodiment of the present invention, the exits of the outer tube 12, which is divided into two tubular sections 15, 16, are respectively wrapped by sterilized cotton swabs or other liquid absorbable attachments 33, 34 which further cover the above-mentioned through holes 19, 20, and the liquid exuding holes 27, 28, for absorbing liquid 90 flowing or oozing out of the inner tube 11.

Figure 5:
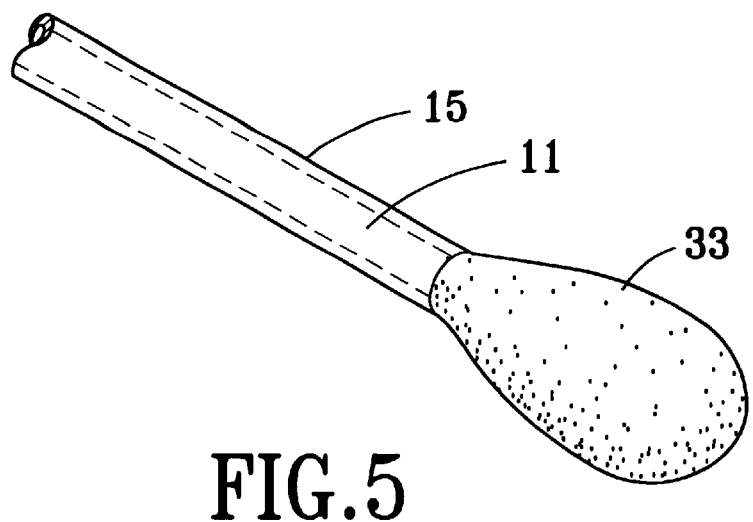
FIG. 5 is a fragmentary three-dimensional view showing that a cotton swab is wrapped around the open end of the container of the present invention.
Figure 6:
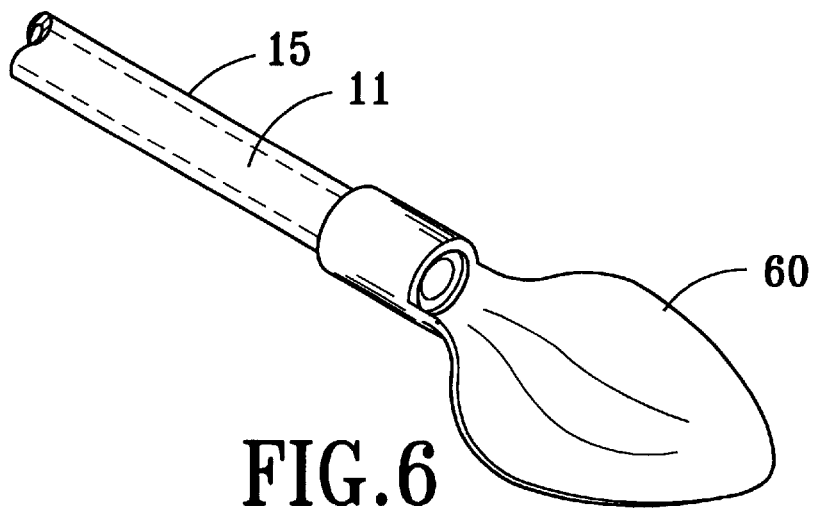
FIG. 6 is a fragmentary three-dimensional view showing that a spoon is attached to the open end of the container of the present invention.
Figure 7:
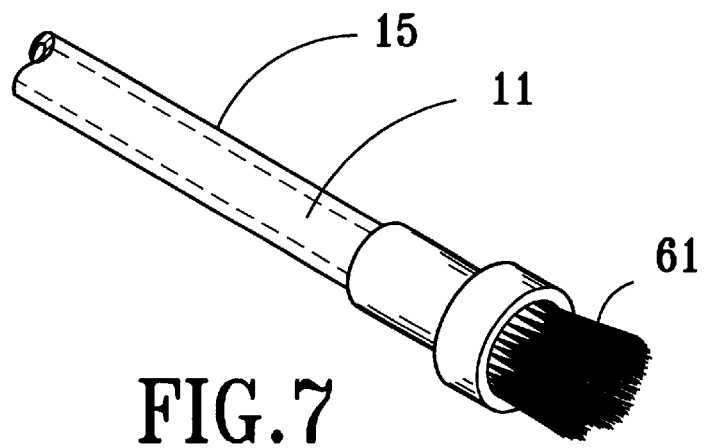
FIG. 7 is a fragmentary three-dimensional view showing that a brush is attached to the exit terminal of the container of the present invention.

The attachments 33, 34 may be in various forms according to their usage; for example, if the cotton swabs are for medical or cosmetic use, the cotton swabs 33, 34 can be wrapped around the exits of the tubular sections 15, 16, as shown in FIG. 5, a spoon 60 for seasonings may be attached as shown in FIG. 6, a brush 61 for cosmetics as shown in FIG. 7, or even a churning stick so as to absorb or accept the liquid content flowing out of the inner tube 11 such as medicines, cosmetics, perfumes, seasonings, food and drinks, and detergents for users to apply on a trauma, for make up, seasoning, cleansing using the attachment 33, 34.

Figure 8:
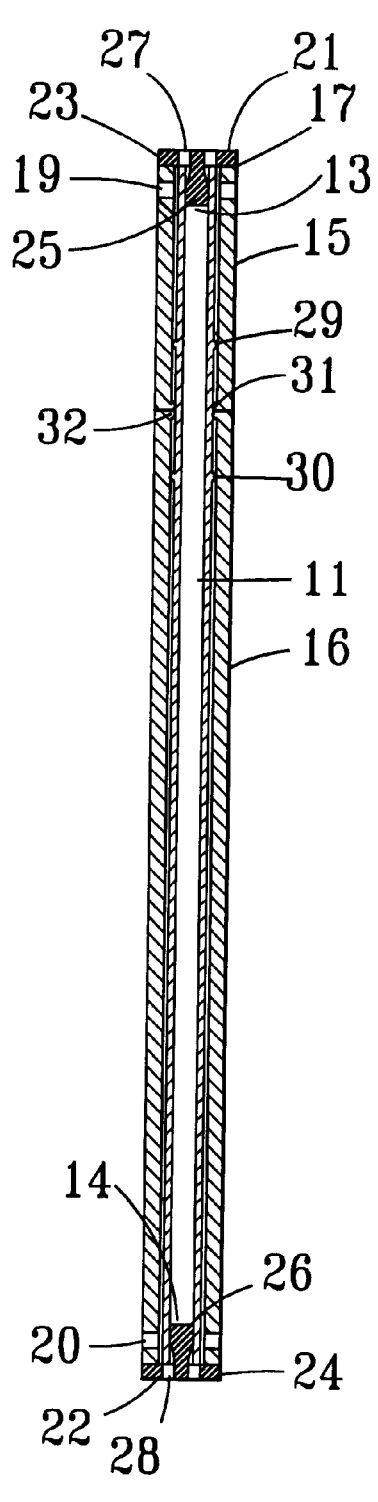
FIG. 8 is a lengthwise cross-sectional view wherein the container is in the closed state in a third embodiment of the present invention.
Figure 9:
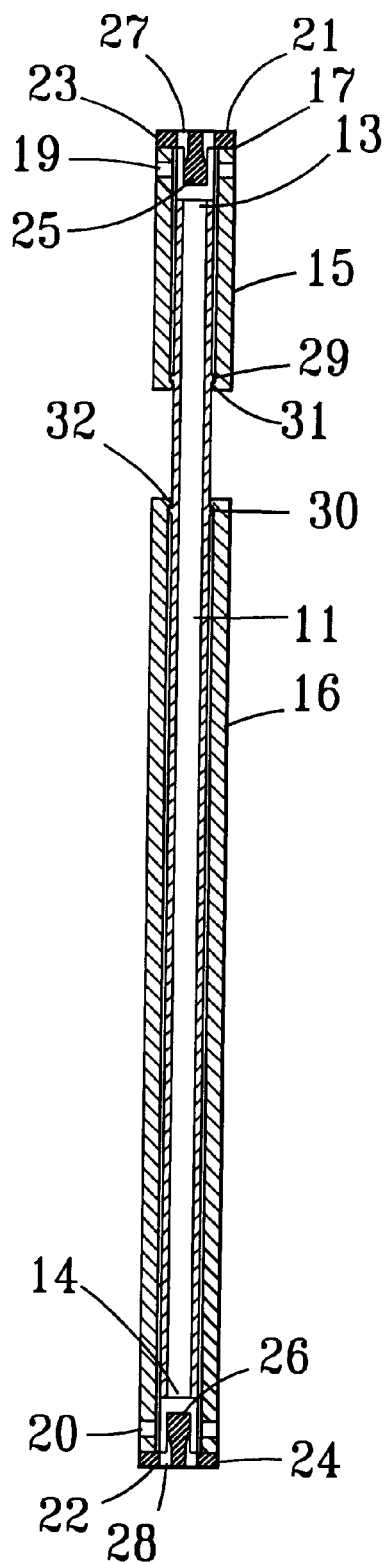
FIG. 9 is a lengthwise cross-sectional view wherein the container is in the opened state in a third embodiment of the present invention.

Referring to FIGS. 8 and 9, in the third embodiment of the present invention, the length of the tubular sections 15, 16 are adjustable and are not limited to an equal length. Skid flanges 29, 30 can be formed at any portion of the inner tube 11, depending on the relation of length between the tubular sections 15 and 16. In other words, the length of the tubular sections 15, 16, and the position of the skid flanges 29, 30, with respect to the positioning flanges 31, 32 on the outer tubular sections 15, 16, can be optionally adjusted and do not have to be limited by the embodiments of the invention shown in the attached drawings.

Figure 10:
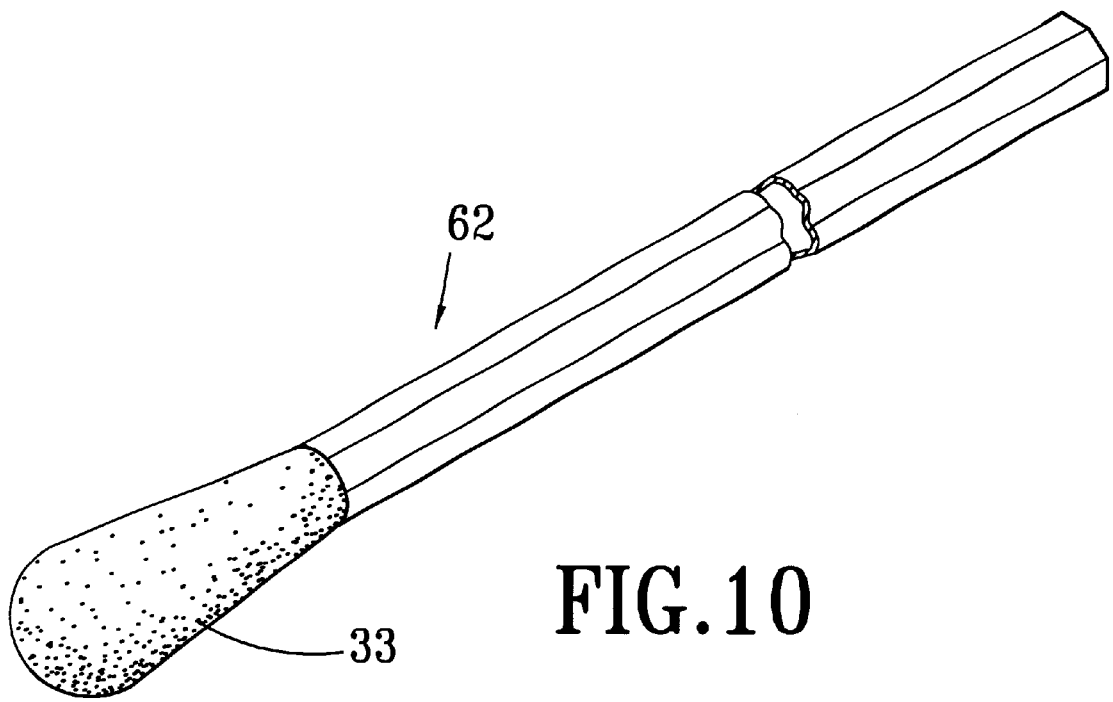
FIG. 10 is a three-dimensional perspective view of a hollow prism shaped container in a fourth embodiment of the present invention.
Figure 11:
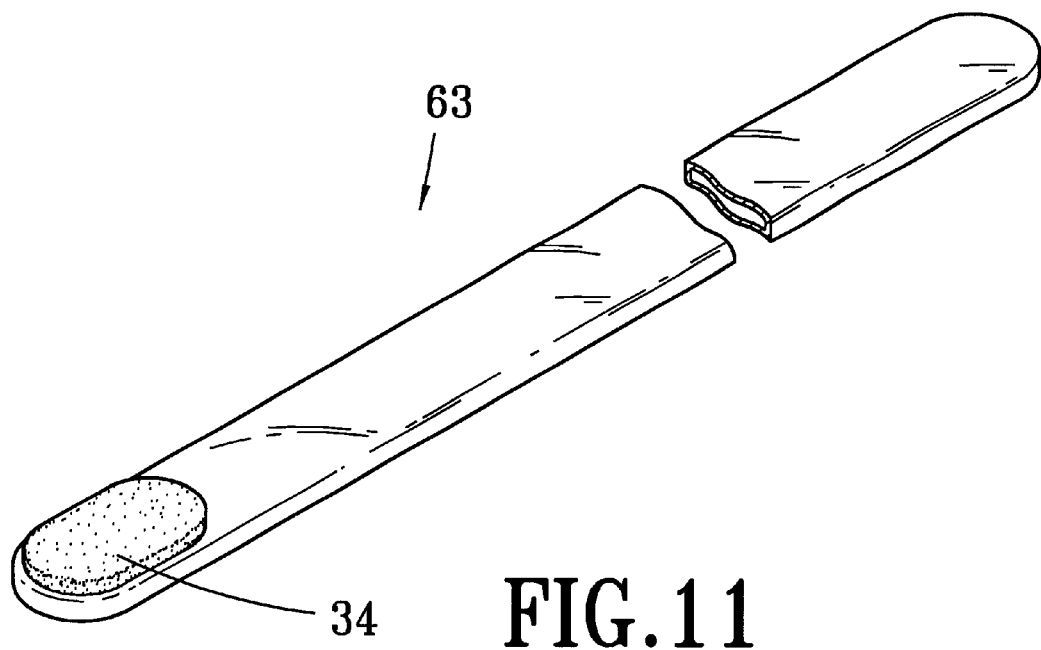
FIG. 11 is a three-dimensional perspective view of a flat hollow rectangular column shaped container in a fifth embodiment of the present invention.

Referring to FIGS. 10 and 11, in the fourth and the fifth embodiments of the present invention, the configuration of the tubular container is not limited to a conventional hollow slender cylinder, it can be formed into a hollow prism shaped container 62, as shown in FIG. 10, or a flat hollow rectangular column-shaped container 63, shown in FIG. 11, or in any other suitable contour. In the embodiment of FIG. 11, the attachment 34 is conjoined on the end surface of the flat column container 63 such that the liquid stored in the inner tube 11 flows out of the through hole bored on the column container 63 and is absorbed by the attachment 34.

Figure 12:
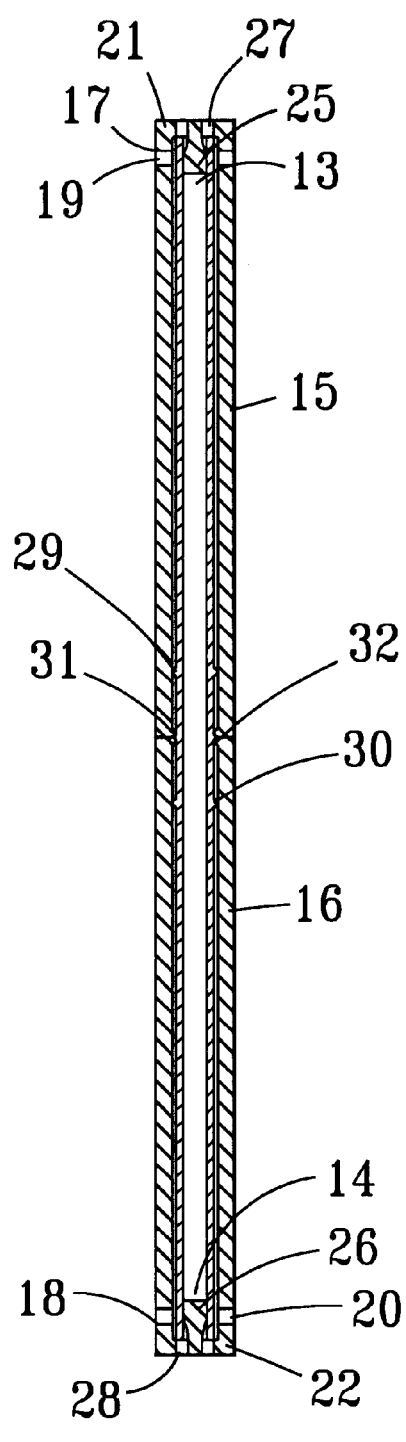
FIG. 12 is a lengthwise cross-sectional view wherein the container is in the closed state in a sixth embodiment of the present invention.
Figure 13:
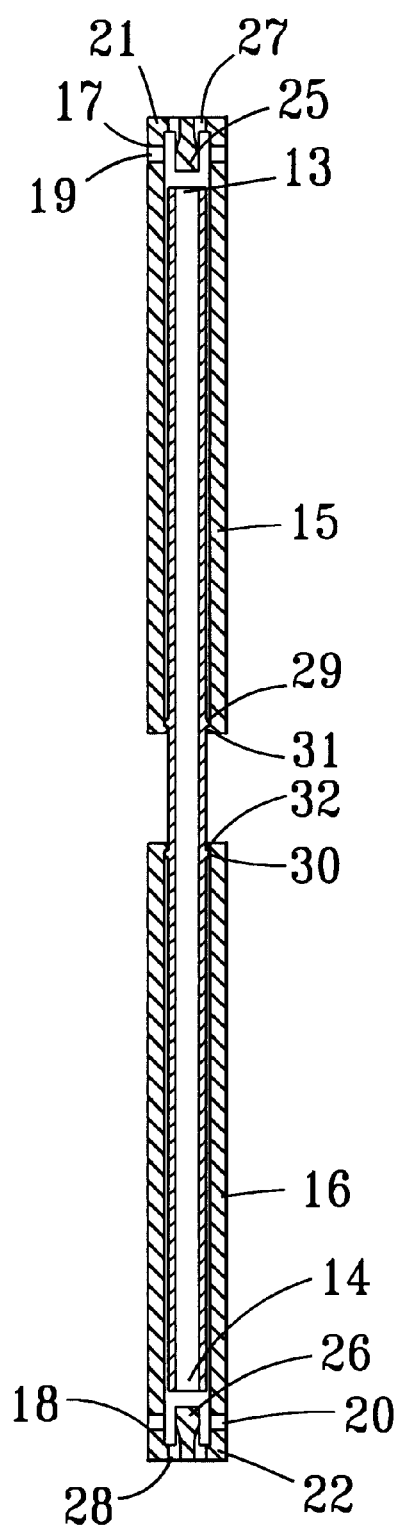
FIG. 13 is a lengthwise cross-sectional view wherein the container is in the opened state in a sixth embodiment of the present invention.

In these two embodiments, the first and the second sealing elements 21, 22 are made independent of tubular sections 15, 16, as in the first and the second embodiments, and then attached together with some proper binding means. Alternatively, the first and the second sealing elements 21, 22 can be formed as one piece, respectively, with the tubular sections 15 and 16, as in the sixth embodiment shown in FIGS. 12 and 13.

Figure 14:
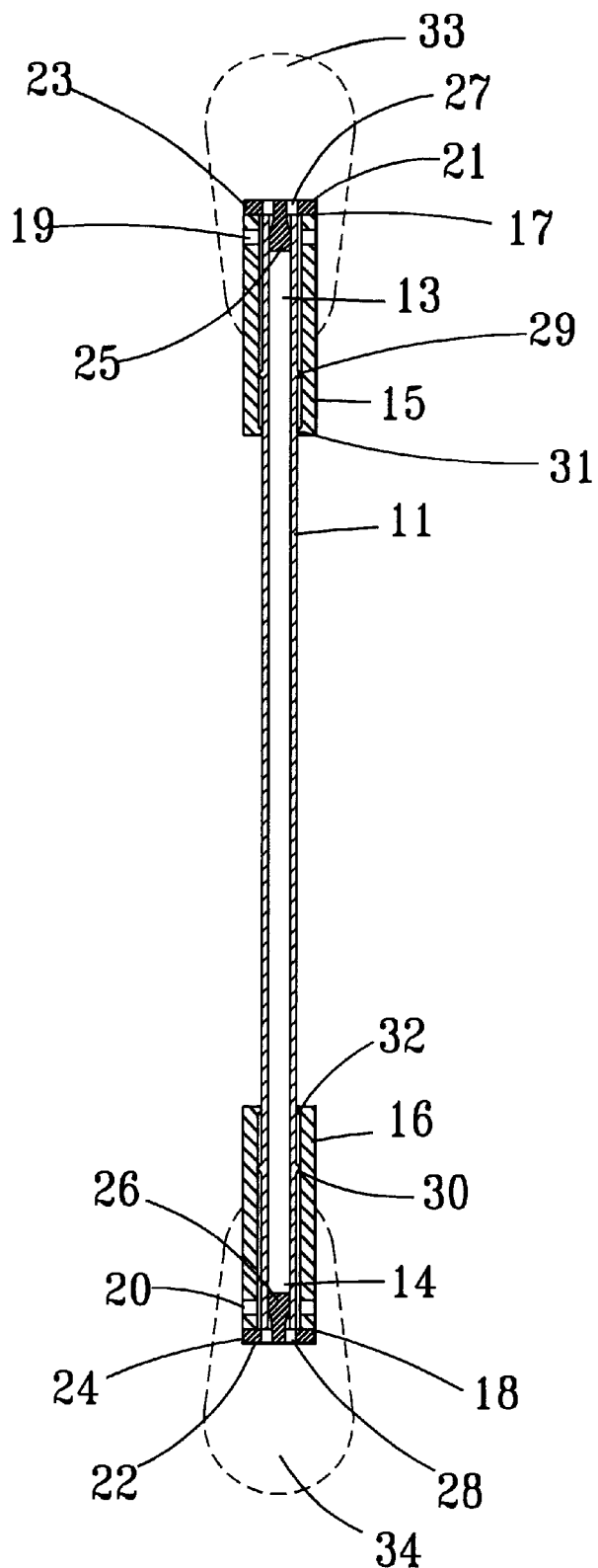
FIG. 14 is a lengthwise cross-sectional view wherein the container is in the closed state in a seventh embodiment of the present invention.

Referring to FIG. 14, in the seventh embodiment of the present invention, the length of tubular sections 15, 16 may be reduced so that they will not mate with each other when they are positioned respectively at the open ends 13 and 14 of the inner tube 11, as shown in FIG. 14.

In the present invention, relative displacement of the tubular sections 15, 16 with respect to the inner tube 11 is not limited only to a horizontal sliding motion, as described in the previous embodiments. Means such as screw threaded motion, wriggling by corrugated pipe, and other equivalent means are applicable.

Figure 15:
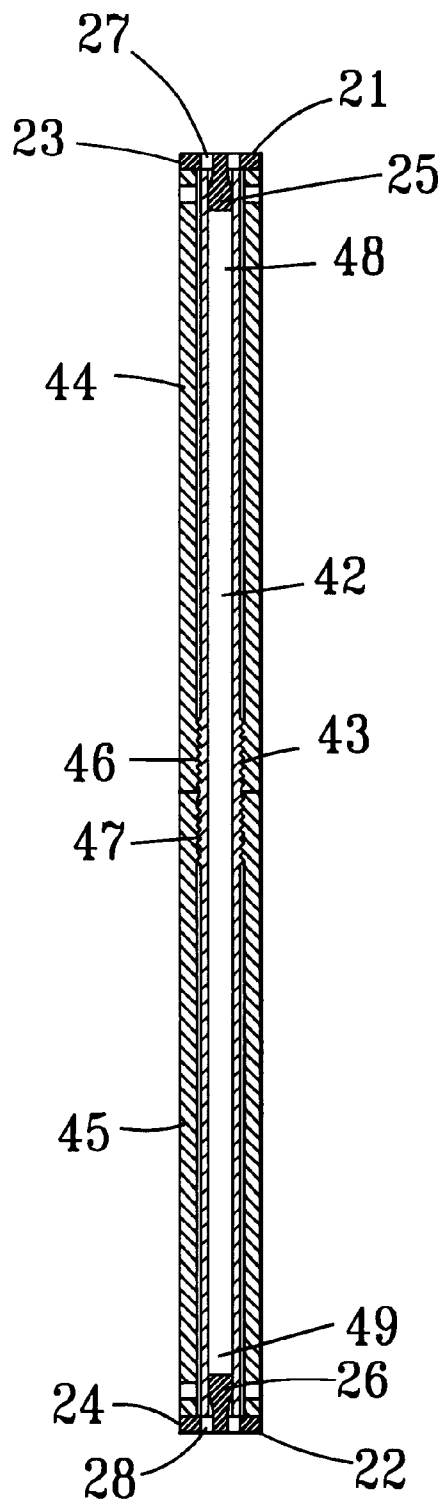
FIG. 15 is a lengthwise cross-sectional view wherein the container is in the closed state in an eighth embodiment of the present invention.

Referring to FIG. 15, in the eighth embodiment of the present invention, one or two outer threaded portions 43 can be provided on the outer wall surface of an inner tube 42 at its center portion, near both ends, or any other portion thereof. On the other hand, inner threaded portions 46 and 47 corresponding to the outer threaded portion 43 are formed respectively on the inner sides at the open ends of tubular sections 44 and 45. By screw threaded motion, the tubular sections 44, 45 can reach the position closing the open ends 48, 49 of the inner tube 42 and, in reverse, be moved away from that position to open the open ends 48, 49.

Figure 16:
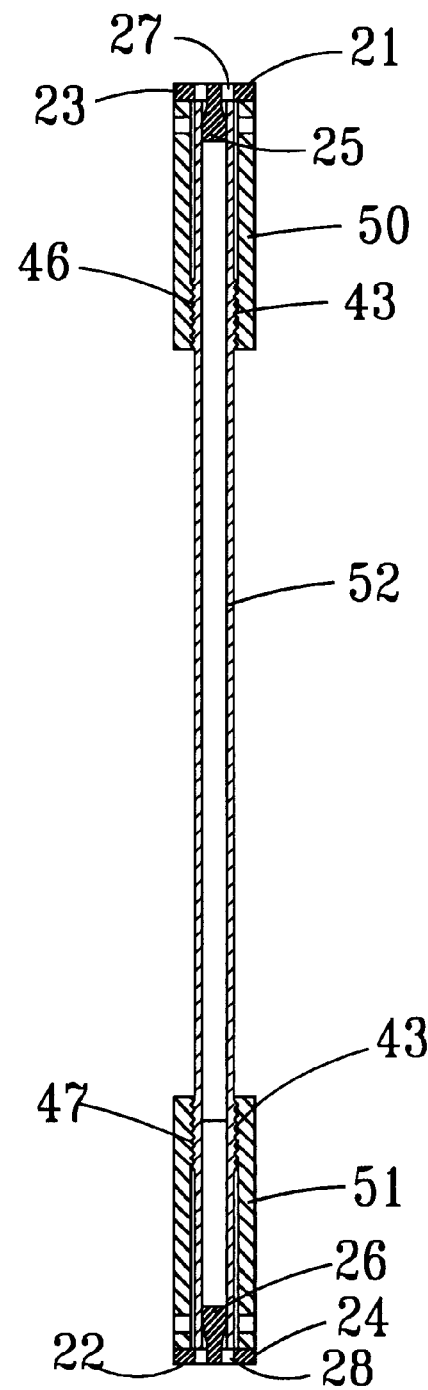
FIG. 16 is a lengthwise cross-sectional view wherein the container is in the closed state in a ninth embodiment of the present invention.

Referring to FIG. 16, in the ninth embodiment of the present invention, the threaded portions 43, 46, 47 can also be provided for relatively displacing the two tubular sections 50, 51 of reduced length, with respect to an inner tube 52, as employed in the eighth embodiment.

Figure 17:
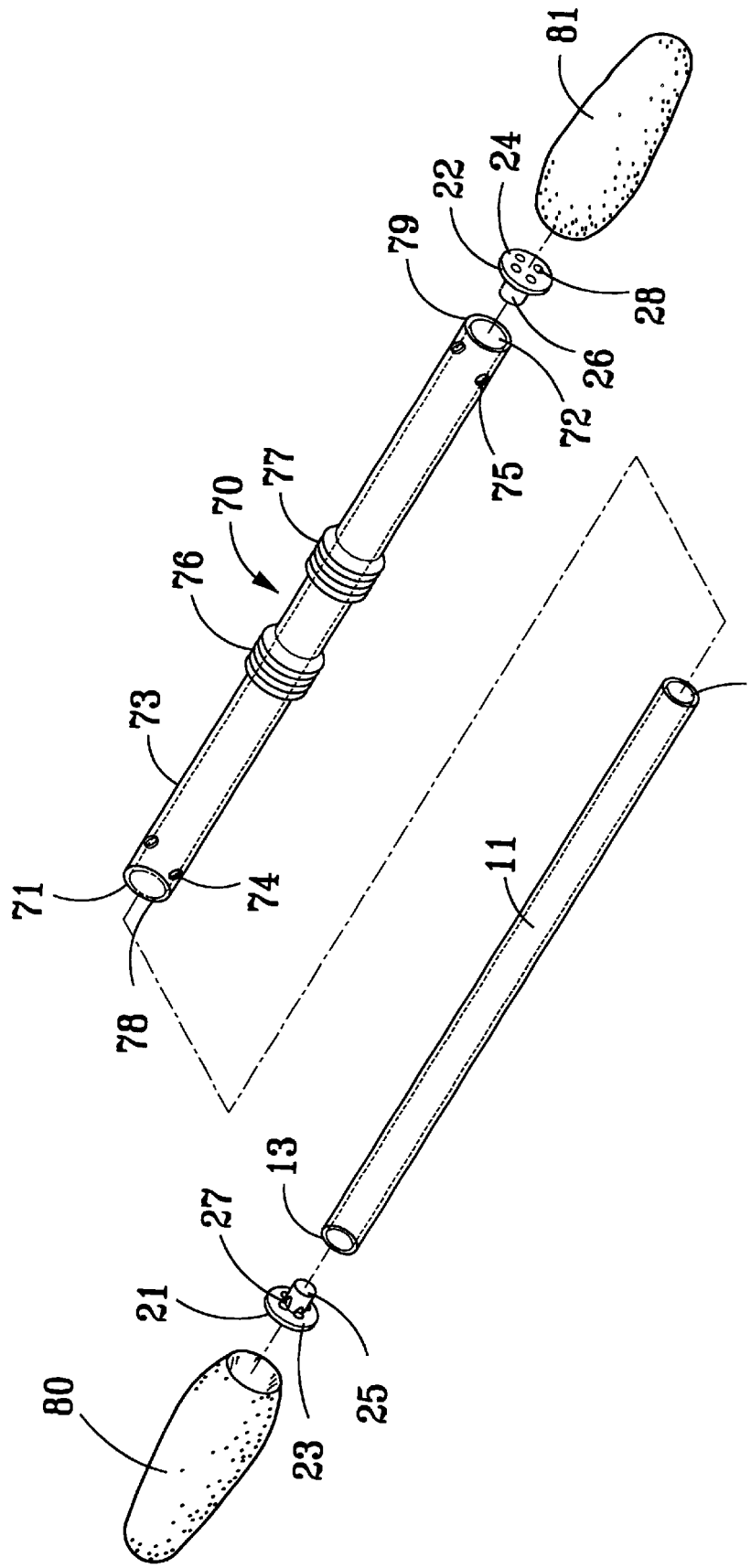
FIG. 17 is a three-dimensional perspective view in a tenth embodiment of the present invention.

FIG. 17 shows a three dimensional view of the tenth embodiment, the container of the present invention comprising an inner tube 11 filled with one of various kinds of liquid; an extendable and shrinkable outer tube 70; first and a second sealing elements 21, 22 for closing open ends 13, 14 of the inner tube 11, respectively; and tools 80, 8 wrapped around or attached to the two ends of the outer tube for absorbing or accepting the liquid.

The extendable and shrinkable outer tube 70 is a hollow tubular body, made of non-poisonous material, having two open ends 71, 72. The inner diameter of the outer tube 70 is slightly greater than the outer diameter of the inner tube 11, allowing the inner tube 11 to be enclosed by the outer tube 70. In addition to two through holes 74, 75 bored on the tube body 73 of the outer tube 70 near the two open ends 71, 72, there are provided more than one expansible portions 76, 77 formed of corrugated pipes or other elastically expansible structure. By pulling or pressing the expansible portions 76, 77 along a lengthwise direction of the tube body 73, the length of the outer tube 70 can be changed accordingly.

The first and second sealing elements 21, 22 are made of non-poisonous rubber or plastic materials whose longitudinal cross-section is formed as a T-shape. The annularly protruded lip portions 23, 24 formed on the top fringes of the first and the second sealing elements 21, 22 extend a width approximately equal to the outer diameter of the expansible outer tube 70. The stem portions 25, 26 of reduced diameter of the first and the second sealing elements 21, 22 are tightly plugged into the two open ends 13, 14 of the inner tube 11, thereby prohibiting the liquid content stored therein to flow out.

Figure 18:
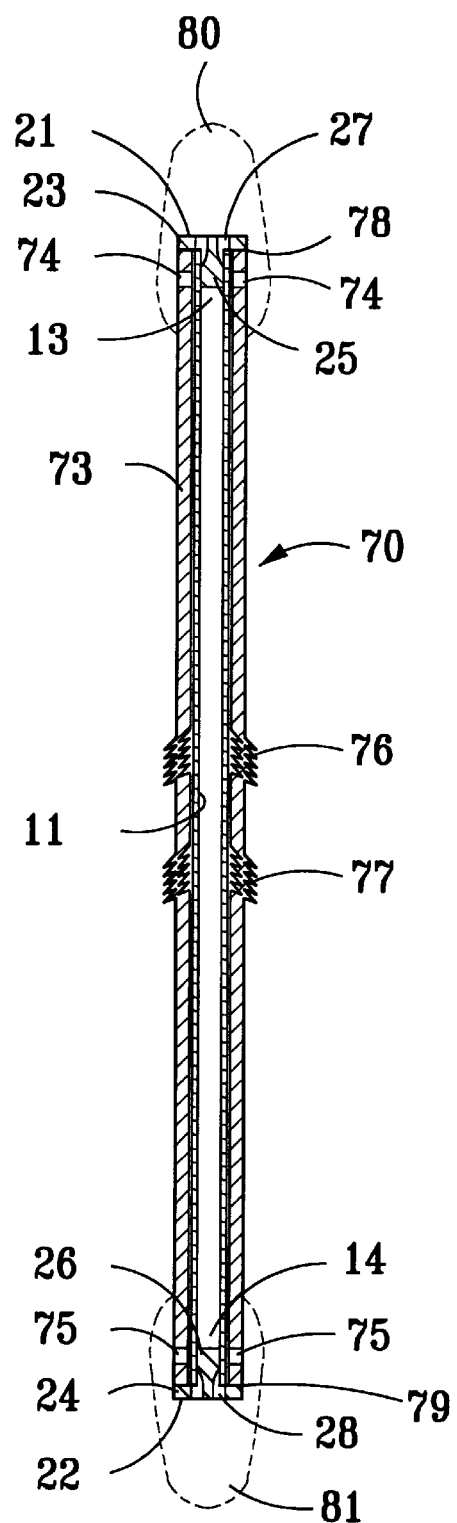
FIG. 18 is a lengthwise cross-sectional view wherein the container is in the closed state in a tenth embodiment of the present invention.

Referring to FIGS. 17 and 18, these two drawings belong to the tenth embodiment of the present invention. In FIG. 17, an extendable and shrinkable outer tube 70 is shrunk to a minimal length, which is almost as long as inner tube 11, when the inner tube 11 is inserted into the outer tube 70 so as to clog two through holes 74, 75 formed on the tube body 73 of the outer tube 70, and also closing a bottom open end 72 of the outer tube 70 with a second sealing element 22. The annularly protruded lip portion 24 of the sealing element 22 is attached to the bottom fringe 79 of the outer tube 70, while the stem portion 26 thereof is plugged into the inner tube 11, thereby closing the bottom open end 14. Then a selected liquid can be filled into the inner tube 11 through the top open end 13 thereof. After the inner tube 11 is filled with the liquid, sealing the top open end 13 of the inner tube 11 with the first sealing element 21, and similarly, attaching the annularly protruded lip portion 23 of the first sealing element 21 at the top fringe 78 of the outer tube 70, the stem portion 25 is plugged into the inner tube 11 so as to close the top open end 13 thereof. Finally, wrapping or attaching tools 80, 81 around or to the openings 71, 72 of the outer tube 70 for absorbing or accepting the liquid. The forms of the tools 80 and 81 can be varied according to the requirements of the user; for example, a sterilized cotton swab wrapped around the open ends 71, 72 or the through holes 74, 75 for absorbing medicines, for other purposes, the tools 80, 81 can be made into spoons, churning sticks or brushes, etc.

In case of need, the annularly protruded lip portions 23, 24 of the first and the second sealing elements 21, 22 may adhere to both top and bottom fringes 78 and 99 through use of a suitable binder so that the first and second sealing elements 21, 22 are firmly attached to the outer tube 70 without the risk of disconnection.

Figure 19:
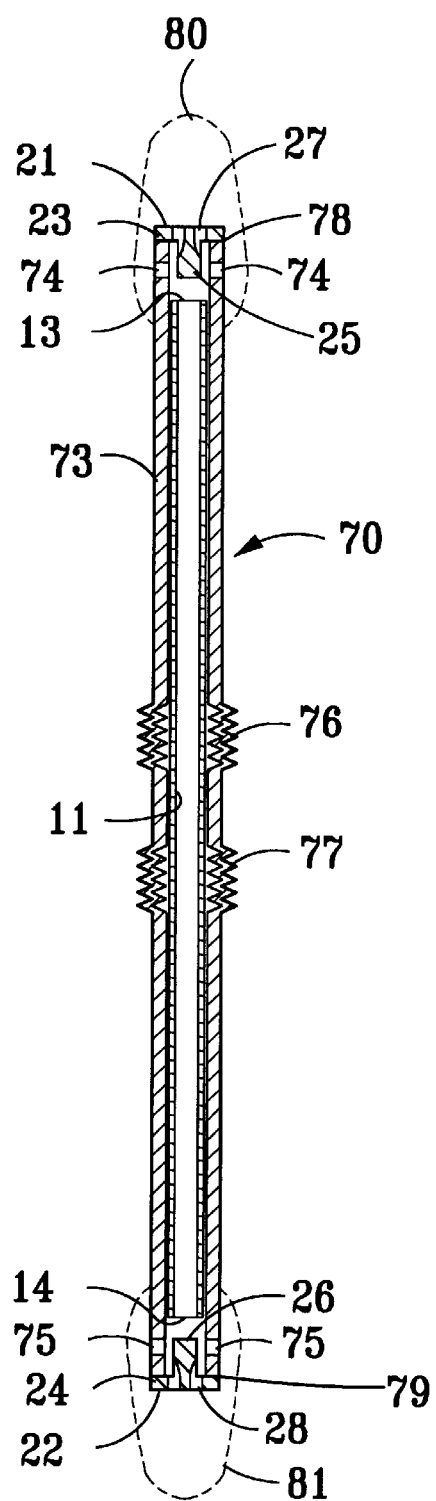
FIG. 19 is a lengthwise cross-sectional view wherein the container is in the opened state in a tenth embodiment of the present invention.

As shown in FIG. 19, if it is intended to take out the content stored in the inner tube 11, the user may pull the outer tube 70 so as to stretch the expansible portions 76, 77 on the tube body 73, thereby the outer tube 70 is elongated together with the two sealing elements 21, 22 and the tools 80, 81. As a result, the sealing elements 21, 22 are separated from the open ends 13 and 14, respectively, at the same time, the through holes 74, 75 provided on the tube body 73 of the outer tube 70 are released from closing the inner tube 11 so that the air confined in the inner tube becomes communicative with the outside via the through holes 74, 75 and the two open ends 13, 14 on the inner tube 11, and the liquid stored in the inner tube 11 is able to flow out automatically via the open ends 13, 14 and the through holes 74, 75 by the outside atmospheric pressure, and is absorbed or accepted by the tools 80, 81 for various application described above.

Referring to FIGS. 17, 18, and 19, the flow rate and flow velocity are controllable by the diameter size of the through holes 74,75. Besides, several through holes 27, 28, which extend from the intermediate position of the stem portions 25, 26 of the sealing elements 21, 22 until puncturing through the annularly protruded lip portions 23, 24, so as to make a pathway for the liquid stored in the inner tube 11 to reach the tools 80, 81 via through holes 27, 28. This group of through holes 27, 28 and the other aforementioned group of through holes 74, 75 can either all be provided or, optionally, provided in any suitable sub-groups.

Figure 20:
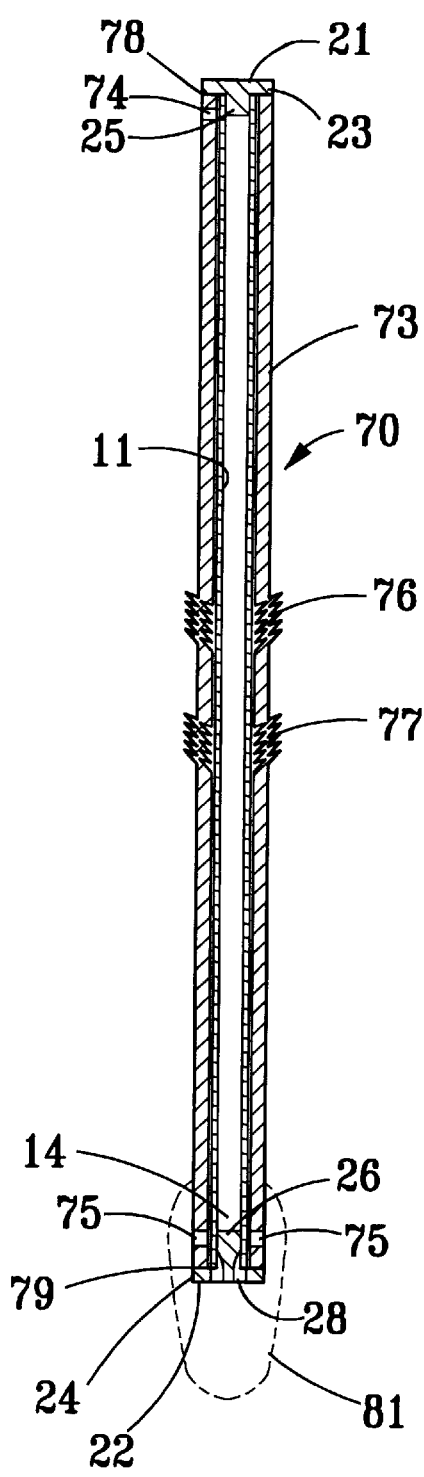
FIG. 20 is a lengthwise cross-sectional view wherein the container is in the closed state in an eleventh embodiment of the present invention.
Figure 21:
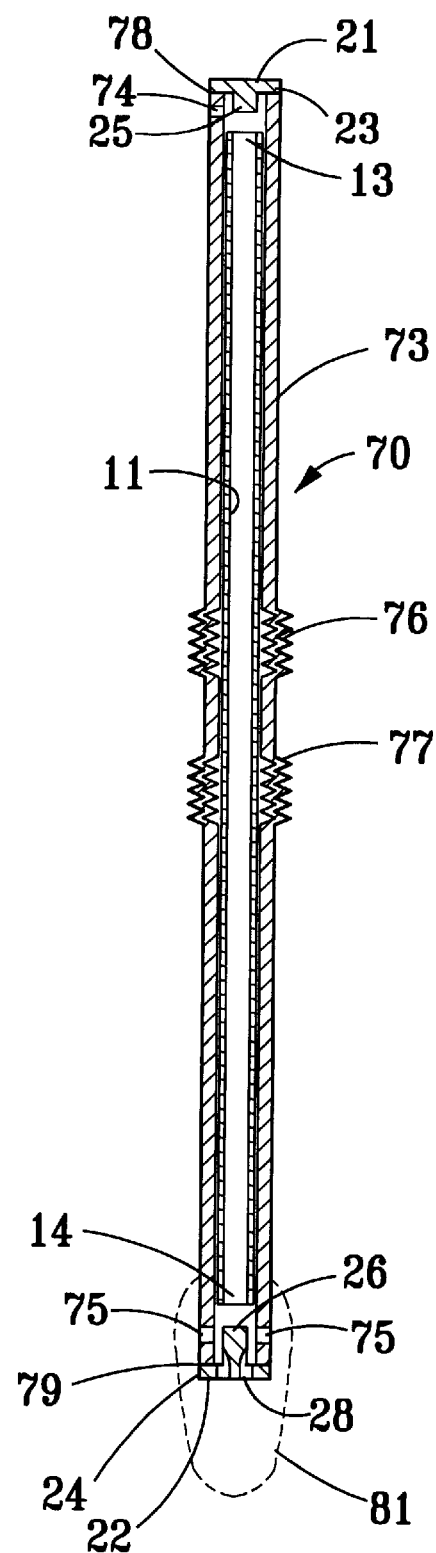
FIG. 21 is a lengthwise cross-sectional view wherein the container is in the opened state in an eleventh embodiment of the present invention.

Referring to FIGS. 20 and 21, in the eleventh embodiment of the present invention, the features thereof are substantially similar to those of the tenth embodiment, wherein the essential difference between the two is that in the eleventh embodiment, there is one attachment (either a wrapped cotton swab or another tool) 81 attached to the bottom end of the extendable and shrinkable outer tube 70 only, other constructions regarding to the inner tube 11, the first and second sealing elements 21, 22, and method of operation being identical to the tenth embodiment.

Now, after having read the above description of selective embodiments, it will be clearly understood that the aforementioned objects of the present invention to provide an easily opened elongated tubular container for storing various kinds of liquid content in completely sealed condition before use, thereby assuring its quality; no limit to the size of tube openings; tools of different types and sizes being optionally selective according to user requirements; and with simple construction can thereby be achieved.

It is therefore to be understood that the above and other modifications and changes may be readily made in the construction and arrangement of elements comprising the preferred and modified forms of invention without departing from the spirit and scope of the invention as defined by the appended Claims and reasonable equivalents thereof. achieved.

It is therefore to be understood that the above and other modifications and changes may be readily made in the construction and arrangement of elements comprising the preferred and modified forms of invention without departing from the spirit and scope of the invention as defined by the appended claims and reasonable equivalents thereof.

What is claimed is:

1. An elongated tubular container comprising:

a hollow inner tube member having opposed open ends; and, first and second hollow outer tube members, each of said hollow outer tube members having an open end and a closed end, each of said closed ends having a stopper member projecting therefrom within an interior of each of said hollow outer tube members, a passage being formed through each of said hollow outer tube members and communicating with said interior, said passage being formed adjacent said closed end, said hollow inner tube member being received within said first and second hollow outer tube members such that said stopper members seal said opposed open ends of said hollow inner tube member, whereby materials stored within said hollow inner tube member may be dispensed through said passages when said first and second hollow outer tube members are pulled apart, thereby removing said stopper members from said opposed open ends of said hollow inner tube member, said hollow inner tube member being resealable when said first and second hollow outer tube members are selectively pushed together.

2. The elongated tubular container as recited in claim 1 wherein each of said stopper members has a substantially T-shaped cross-section.

3. The elongated tubular container as recited in claim 2 wherein said stopper member is formed separately from said hollow outer tube member and is adhered thereto.

4. The elongated tubular container as recited in claim 2 wherein said stopper member and said hollow outer tube member are formed in one-piece formation.

5. The elongated tubular container as recited in claim 2 wherein said stopper member has a liquid exuding hole formed therethrough.

6. The elongated tubular container as recited in claim 1 wherein at least one attachment is fixed to each of said hollow outer tube members about said closed ends thereof for absorbing said material.

7. The elongated tubular container as recited in claim 6 wherein said attachment is a sterilized cotton swab.

8. The elongated tubular container as recited in claim 6 wherein said attachment is a brush.

9. The elongated tubular container as recited in claim 6 wherein said attachment is a spoon.

10. The elongated tubular container as recited in claim 1 wherein each of said first and second hollow outer tube members has an inwardly extended positioning flange projecting within said interior thereof and said hollow inner tube member has a skid flange projecting outwardly therefrom, said skid flange and said inwardly extended positioning flange engaging one another and displacing said hollow inner tube member from said hollow outer tube members when said hollow outer tube members are pulled apart.

11. The elongated tubular container as recited in claim 1 wherein said hollow inner tube member is threadedly secured to said first and second hollow outer tube members.

12. The elongated tubular container as recited in claim 1 wherein each of said hollow outer tube members has an extendable portion such that said hollow outer tube members may be elongated or compressed.

13. The elongated tubular container as recited in claim 12 wherein said expandable portion is formed of a corrugated soft pipe.

14. The elongated tubular container as recited in claim 1 wherein said first and second hollow outer tube members have different lengths.

15. The elongated tubular container as recited in claim 14 wherein said first and second hollow outer tube members mate with one another.

* * * * *